United States Patent [19]

Scharf

[11] Patent Number: 5,990,162
[45] Date of Patent: Nov. 23, 1999

[54] METHOD FOR TREATMENT OF FIBROMYALGIA AND CHRONIC FATIGUE SYNDROME

[75] Inventor: Martin B. Scharf, Cincinnati, Ohio

[73] Assignee: Orphan Medical, Inc., Minnetonka, Minn.

[21] Appl. No.: 08/920,979

[22] Filed: Aug. 29, 1997

[51] Int. Cl.⁶ .................................................. A61K 31/235
[52] U.S. Cl. ........................... 514/533; 514/923; 424/449
[58] Field of Search ..................................... 514/529, 557, 514/533; 424/449

[56] References Cited

U.S. PATENT DOCUMENTS

| | | | |
|---|---|---|---|
| 4,599,355 | 7/1986 | Kluger et al. | 514/533 |
| 4,738,985 | 4/1988 | Kluger et al. | 514/533 |
| 5,594,030 | 1/1997 | Conte et al. | 514/553 |

FOREIGN PATENT DOCUMENTS

| | | | |
|---|---|---|---|
| 0561408 | 9/1993 | European Pat. Off. | |
| 95/017989 | 1/1995 | WIPO. | |
| 96/40105 | 12/1996 | WIPO | A61K 31/19 |

OTHER PUBLICATIONS

*The Facts About Chronic Fatigue Syndrome*, Centers for Disease Control and Prevention, National Center for Infectious Diseases, Atlanta, GA, 1–21, (Mar. 1995).

Bennett, R.M., et al., "Hypothalamic–Pituitary–Insulin–like Growth Factor–I Axis Dysfunction in Patients with Fibromyalgia", *The Journal of Rheumatology*, 24, 1384–1389, (1997).

Buchwald, D., et al., "Insulin–like Growth Factor–I (Somatomedin C) Levels in Chronic Fatigue Syndrome and Fibromyalgia", *The Journal of Rheumatology*, 23, 739–742, (1996).

Entholzner, E., et al., "EEG Changes During Sedation with Gamma–Hydroxybutyric Acid", *Anaesthesist*, 44 (5), 345–350, (1995).

Fukuda, K., et al., "Management Strategies for Chronic Fatigue Syndrome", *Federal Practitioner*, 9 pgs, (Jul. 1995).

Goldenberg, D.L., et al., "A Randomized, Controlled Trial of Amitriptyline and Naproxen in the Treatment of Patients With Fybromyalgia", *Arth. Rheum.*, 29, 1371, (1986).

Goldenberg, D.L., et al., "Fibromyalgia and Chronic Fatigue Syndrome: Are they the Same?", *J. Muscoloskel Med.*, 7, 19, (1990).

Goldenberg, D.L., et al., "High Frequency of Fibromyalgia in Patients with Chronic Fatigue Seen in a Primary Care Practice", *Arth. Rheum.*, 33 (3), 381–387, (Mar. 1990).

Griep, E.N., et al., "Pituitary Release of Growth Hormone and Prolactin in the Primary Fibromyalgia Syndrome", *The Journal of Rheumatology*, 21, 2125–2130, (1994).

Mamelak, M., et al., "The Effects of Gamma–Hydroxybutyrate on Sleep", *Biol. Psychiatry*, 12 (2), 273–288, (1977).

Moldofsky, H.D., et al., "A Chronbiologic Theory of Fibromyalgia", *J. Muscoloskel. Pain, 1,* 49, (1993).

Moldofsky, H.D., et al., "Musculoskeletal Symptoms and Non–REM Sleep Disturbance in Patients with "Fibrositis Syndrome" and Healthy Subjects", *Psychosoma. Med.,* 37, 341, (1975).

Pellegrino, M.J., et al., "Familial Occurrence of Primary Fibromyalgia", *Arch. Phys. Med. Rehab.*, 70, 61, (1989).

Schaefer, K.M., "Sleep Disturbances and Fatigue in Women With Fibromyalgia and Chronic Fatigue Syndrome", *JOGNN,* 24 (3), 229–233, (Mar./Apr. 1995).

Scharf, M.B., et al., "Current Pharmacologic Management of Narcolepsy", *American Family Physician,* 38 (1), 143–148, (Jul. 1988).

Scharf, M.B., et al., "The Effects and Effectiveness of y–Hydroxybutyrate in Patients with Narcolepsy", *J. Clin. Physchiatry,* 46 (6), 222–225, (1985).

Smythe, H.A., "Studies of Sleep in Fibromyalgia: Techniques, Clinical Significance, and Future Directions", *British Journal of Rheumatology,* 34, 897–900, (1995).

Van Cauter, E., et al., "Simultaneous Stimulation of Slow–Wave Sleep and Growth Hormone Secretion by Gamma–hydroxybutyrate in Normal Young Men", *J. Clin. Invest.,* 100 (3), 745–753, (1997).

Yamada, Y., et al., "Effect of Butyrolactone and Gamma–Hydroxybutyrate on the EEG and Sleep Cycle in Man", *Electroenceph. clin. Neurophysiol.,* 22, 558–562, (1967).

Yunus, M.B., et al., "A Controlled Study of Primary Fibromyalgia Syndrome: Clinical Features and Association with Other Functional Syndromes", *J. Rheumatol.,* 16, 62, (1989).

Broughton, R., et al., "The Treatment of Narcolepsy–Cataplexy with Nocturnal Gamma–Hydroxybutyrate", *Le Journal Canadian des Sciences Neurologiques,* 6 (1), 285–289, (1979).

Mamelak, M., et al., "Treatment of Narcolepsy with y–Hydroxybutyrate. A Review of Clinical and Sleep Laboratory Findings", *Sleep,* 9(1), 285–289, (1986).

Montplaisir, J., et al., "Le Gamma–hydroxybutyrate de Sodium (GHB) dans le Traitement de L'hypersomnie Essentielle", *Can. J. Psychiatry,* 26, 162–166, (1981).

CA 126:99858 Van Cauter et al Jun. 1996.

CA 127:200274 Van Cauter et al 1997.

CA 87:112300 1977 M. Mamelak et al.

CA 123:188258 (1995).

*Primary Examiner*—Peter F. Kulkosky
*Attorney, Agent, or Firm*—Schwegman, Lundberg, Woessner and Kluth

[57] ABSTRACT

A method is provided to treat a human afflicted with chronic fatigue syndrome or fibromyalgia syndrome by the administration of certain butyrate derivatives.

15 Claims, No Drawings

METHOD FOR TREATMENT OF FIBROMYALGIA AND CHRONIC FATIGUE SYNDROME

BACKGROUND OF THE INVENTION

An estimated 6 million Americans suffer the often baffling symptoms of fibromyalgia or chronic fatigue syndrome. Patients with fibromyalgia, also referred to as fibromyalgia syndrome, FMS or fibrositis syndrome, report widespread musculoskeletal pain, chronic fatigue, and non-restorative sleep, and show specific regions of localized tenderness in the absence of demonstrable anatomic or biochemical pathology. Typically, they describe light and/or restless sleep. They awaken feeling unrefreshed with pain, stiffness, physical exhaustion, and lethargy. See, H. D. Moldofsky et al., *J. Muscoloskel. Pain*, 1, 49 (1993). In a series of studies, Moldofsky's group has shown that aspects of the patients' sleep pathology are related to their pain and mood symptoms. That is, patients with fibrositis syndrome show an alpha (7.5 to 11 Hz) electroencephalographic (EEG), non-rapid-eye-movement (NREM) sleep anomaly correlated with musculoskeletal pain and altered mood. Moldofsky has interpreted this alpha EEG NREM sleep anomaly to be an indicator of an arousal disorder within sleep associated with the subjective experience of non-restorative sleep. See H. D. Moldofsky et al., *Psychosom. Med.*, 37, 341 (1975).

Fibromyalgia patients frequently report symptoms similar to those of patients with post-infectious neuromyasthenia, also referred to as chronic fatigue syndrome (CFS). Chronic fatigue syndrome, or CFS, is a debilitating disorder characterized by profound tiredness or fatigue. Patients with CFS may become exhausted with only light physical exertion. They often must function at a level of activity substantially lower than their capacity before the onset of illness. In addition to these key defining characteristics, patients generally report various nonspecific symptoms, including weakness, muscle aches and pains, excessive sleep, malaise, fever, sore throat, tender lymph nodes, impaired memory and/or mental concentration, insomnia, and depression. CFS can persist for years. Compared with fibromyalgia patients, chronic fatigue patients have similarly disordered sleep, localized tenderness, and complaints of diffuse pain and fatigue.

The presence of considerable symptom overlap in FMS and chronic fatigue syndrome has led to speculation that they may represent different facets of the same underlying, as yet unknown disease process (D. L. Goldenberg, *J. Muscoloskel. Med.*, 7, 19 (1990); D. L. Goldenberg, *Arth. Rheum.*, 33, 1132 (1990); M. B. Yunus, *J. Rheumatol.*, 16 (S19), 62 (1989)). Although no specific inheritance pattern has been identified, an increased incidence in relatives of affected patients has been noted (M. J. Pellegrino et al., *Arch. Phys. Med. Rehab.*, 70, 61 (1989)). Development of the syndrome may require a predisposing factor, possibly inherited, as well as a precipitating factor, perhaps something disturbing sleep.

Amitriptyline can be an effective medication for FMS but it also has frequent side effects when used in doses sufficient to keep FMS symptoms well controlled. Particularly bothersome are weight gain, dry mouth, and daytime cognitive impairment. See, D. L. Goldenberg et al., *Arth. Rheum.*, 29, 1371 (1986). Diphenhydramine and trazodorie are in common use because they seem effective and have less side effects, but have not been proven to work in controlled, blinded trials. It is often necessary to try several different medications in succession before finding one that works well with acceptable side effects. Some tolerance develops to the sedative effect of many of these medications, necessitating one or two dose increases after an initial good response to maintain it. There is no pharmacological therapy recognized as effective for CFS.

Therefore, a need exists for an effective drug-based treatment of FMS and/or chronic fatigue syndrome that does not exhibit undue side effects.

SUMMARY OF THE INVENTION

The present invention provides a therapeutic method to treat fibromyalgia syndrome (FMS) or chronic fatigue syndrome (CFS) comprising administering to a patient afflicted with FMS or CFS an effective amount of a compound of formula (I)

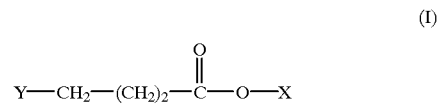

wherein X is H, a pharmaceutically acceptable cation or $(C_1-C_4)$alkyl, and Y is hydroxy, $(C_1-C_4)$alkoxy, $(C_1-C_4)$ alkanoyloxy, or benzoyloxy. The amount of one or more of the compounds of formula (I) is effective to eliminate or alleviate at least one of the symptoms of FMS or CFS. As noted above, such symptoms include, but are not limited to, musculoskeletal pain and weakness, chronic fatigue, including physical exhaustion and lethargy, non-restorative sleep and/or excessive sleep, and regions of localized tenderness in the absence of demonstrable anatomic or biochemical pathology.

Preferred compounds of formula I include the alkali metal salts of 4-hydroxybutyric acid, such as 4-hydroxybutanoic acid monosodium salt (GHB) and the $(C_1-C_2)$alkyl esters of 4-acetoxybutanoic acid or 4-benzoyloxybutanoic acid. Other compounds that can be used in the present methods include those disclosed in Kluger (U.S. Pat. Nos. 4,599,355 and 4,738,985).

DETAILED DESCRIPTION OF THE INVENTION

Gamma-hydroxybutyrate is a naturally occurring substance found in the human nervous system and other organs. It is found in highest concentrations in the hypothalamus and basal ganglia. The discovery of central recognition sites with high affinity for this metabolite suggests that it functions as a neurotransmitter or neuromodulator rather than as an incidental breakdown product of gamma-aminobutyric acid metabolism.

In healthy human volunteers, low doses (about 30 mg/kg) of 4-hydroxybutanoic acid monosodium salt (sodium oxybate or GHB; Merck Index 8603) promote a normal sequence of NREM and REM sleep lasting about 2–3 hours. The most consistent effect observed in patients after GHB administration is an increase in Slow Wave sleep (SWS). Total nocturnal REM sleep duration is usually unchanged. Total sleep time at night may be increased or unchanged. Narcoleptic patients have not shown tolerance to the hypnotic actions of GHB over a 6-month period.

Studies by R. Broughton and M. Mamelak, *Can. J. Neur. Sci.*, 7, 23 (1980), L. Scrima et al., *Sleep*, 13, 479 (1990), and M. B. Scharf et al., *Am. Fam. Phys.*, 143 (July 1988) have evaluated the effects of GHB in the treatment of narcolepsy. The results of these studies confirm that GHB treatment substantially reduces the signs and symptoms of narcolepsy (e.g., daytime sleepiness, cataplexy, sleep paralysis and hypnagogic hallucinations). In addition, GHB increases total sleep time and REM sleep, and decreases REM latency. Results of these studies show a positive safety profile for GHB when used long-term for the treatment of narcolepsy. Adverse experiences with GHB have been minimal in incidence and degree of severity and include episodes of sleepwalking, enuresis, headache, and dizziness.

GHB is available from the Aldrich Chemical Co., Milwaukee, Wis., and can be employed to prepare other compounds within the scope of formula (I). The compound can be esterified with ($C_1$–$C_4$)alkanols and alkanoylated or benzoylated with alkanoyl and benzoyl chloride or anhydrides. The cation can also be readily exchanged to replace sodium with other metal or organic cations, such as $Ca^+$, $K^+$, $Li^+$, or $(R)_4N^+$ wherein each R is H, phenyl, ($C_1$–$C_6$)alkyl or hydroxy($C_1$–$C_6$)alkyl, i.e., ammonium or hydroxyethyl amine salts. For preparation methods for 4-hydroxybutanoic acid and its derivatives, see, Marvel et al., *J. Am. Chem. Soc.*, 51, 260 (1929); Japanese patent 63174947, German Pat. Nos. 237310, 237308 and 237309.

Administration and Dosages

While it is possible that, for use in therapy, the compounds of formula (I), such as 4-hydroxybutyric acid salts, may be administered as the pure chemicals, as by inhalation of a fine powder via an insufflator, it is preferably to present the active ingredient as a pharmaceutical formulation. The invention thus further provides a pharmaceutical formulation comprising a compound of formula (I), together with one or more pharmaceutically acceptable carriers therefor and, optionally, other therapeutic and/or prophylactic ingredients. The cations and carrier(s) must be "acceptable" in the sense of being compatible with the other ingredients of the formulation and not deleterious to the recipient thereof.

Pharmaceutical formulations include those suitable for oral or parenteral (including intramuscular, subcutaneous and intravenous) administration. Forms suitable for parenteral administration also include forms suitable for administration by inhalation or insufflation or for nasal, or topical (including buccal, rectal, vaginal and sublingual) administration. The formulations may, where appropriate, be conveniently presented in discrete unit dosage forms and may be prepared by any of the methods well known in the art of pharmacy. Such methods include the step of bringing into association the active compound with liquid carriers, solid matrices, semi-solid carriers, finely divided solid carriers or combinations thereof, and then, if necessary, shaping the product into the desired delivery system.

Pharmaceutical formulations suitable for oral administration may be presented as discrete unit dosage forms such as hard or soft gelatin capsules, cachets or tables each containing a predetermined amount of the active ingredient; as a powder or as granules; as a solution, a suspension or as an emulsion; or in a chewable base such as a synthetic resin or chicle for ingestion of the active ingredient from a chewing gum. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art, i.e., with enteric coatings.

Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, flavoring, emulsifying agents, non-aqueous vehicles (which may include edible oils), or preservatives.

The compounds according to the invention may also be formulated for parenteral administration (e.g., by injection, for example, bolus injection or continuous infusion) and may be presented in unit dose form in ampules, pre-filled syringes, small volume infusion containers or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g., sterile, pyrogen-free water, before use.

For topical administration to the epidermis, compound(s) of formula (I) may be formulated as ointments, creams or lotions, or as the active ingredient of a transdermal patch. Suitable transdermal delivery systems are disclosed, for example, in A. Fisher et al. (U.S. Pat. No. 4,788,603), Chien et al. (U.S. Pat. No. 5,145,682) or R. Bawa et al. (U.S. Pat. Nos. 4,931,279, 4,668,506 and 4,713,224). Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredient can also be delivered via iontophoresis, e.g., as disclosed in U.S. Pat. Nos. 4,140,122, 4,383,529, or 4,051,842.

Formulations suitable for topical administration in the mouth include unit dosage forms such as lozenges comprising active ingredient in a flavored base, usually sucrose and acadia or tragacanth; pastilles comprising the active ingredient in an inert base such as gelatin and glycerin or sucrose and acacia; mucoadherent gels, and mouthwashes comprising the active ingredient in a suitable liquid carrier.

When desired, the above-described formulations can be adapted to give sustained release of the active ingredient employed, e.g., by combination with certain hydrophilic polymer matrices, e.g., comprising natural gels, synthetic polymer gels or mixtures thereof.

Pharmaceutical formulations suitable for rectal administration wherein the carrier is a solid are most preferably presented as unit dose suppositories. Suitable carriers include cocoa butter and other materials commonly used in the art, and the suppositories may be conveniently formed by admixture of the active compound with the softened or melted carrier(s) followed by chilling and shaping in molds.

Formulations suitable for vaginal administration may be presented as pessaries, tampons, creams, gels, pastes, foams or sprays containing, in addition to the active ingredient, such carriers as are known in the art to be appropriate.

For administration by inhalation, the compounds according to the invention are conveniently delivered form an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the compounds according to the invention may take the form of a dry powder composition, for example, a powder mix of the compound and a suitable powder base such as lactose or starch. The powder composition may be presented in unit dosage form in, for example, capsules or cartridges or, e.g., gelatin or blister packs from which the powder may be administered with the aid of an inhalator or insufflator.

For intra-nasal administration, the compounds of the invention may be administered via a liquid spray, such as via a plastic bottle atomizer. Typical of these are the Mistometer® (Wintrop) and the Medihaler® (Riker).

The pharmaceutical compositions according to the invention may also contain other adjuvants such as flavorings, colorings, antimicrobial agents, or preservatives.

It will be further appreciated that the amount of the compound of formula (I) required for use in treatment will vary not only with the particular compound selected but also with the route of administration, the severity of the condition being treated and the age and condition of the patient and will be ultimately at the discretion of the attendant physician or clinician.

In general, however, a suitable dose will be in the range of that shown to be effective as a hypnotic agent, i.e., to treat narcolepsy, of from about 1–500 mg/kg, e.g., from about 10–250 mg/kg of body weight per day, such as 25 to about 200 mg per kilogram body weight of the recipient per day.

The compound is conveniently administered in unit dosage form; for example, containing 0.5–20 g, conveniently 1–7.5 g, most conveniently, 2–5 g, of active ingredient per unit dosage form.

The total daily dosage, i.e., of about 1–20 g, may be administered for about 1–4 months or longer, as needed.

The desired dose may conveniently be presented in a single dose or as divided doses administered at appropriate intervals, for example, as two, three, four or more doses or sub-doses per day. The sub-dose itself may be further divided, e.g., into a number of discrete loosely spaced administrations; such as teaspoons of a liquid composition or multiple inhalations from an insufflator.

The invention will be further described by reference to the following detailed Example.

During the course of open label investigation of the effects of sodium oxybate (GHB) in narcoleptic patients (IND 21,654) GHB was administered to three patients with the concurrent diagnoses of narcolepsy and fibromyalgia (2 patients) or chronic fatigue syndrome (1 patient). In each case the narcoleptic auxiliary symptoms improved as expected. Moreover, the symptoms of their secondary diagnoses also improved dramatically, possibly in association with the GHB-induced changes in slow wave sleep (stage 3 & 4). Therefore, the effects of sodium oxybate (GHB) were evaluated on the sleep patterns and clinical symptoms of non-narcoleptic patients with previously diagnosed fibromyalgia and/or chronic fatigue syndrome.

Example 1

Use of GHB to Treat Fibromyalgia or Chronic Fatigue Syndrome

I. SUBJECT SELECTION

A. Inclusion Criteria

Each subject met the following criteria prior to entering the study:

1. Four patients with a previously confirmed diagnosis of fibromyalgia including one with a confirmed diagnosis of chronic fatigue syndrome were evaluated in this open label unblinded pilot study.

2. An overnight polysomnography was performed to rule out other sleep disorders as the cause of non-restorative sleep. Clinically significant levels of Sleep Apnea (RDI->15 episodes/hour) or Periodic Limb Movements in Sleep (>15 episodes per hour with arousals) were exclusionary unless polysomnography confirms that the disorder is under adequate therapeutic control (i.e., RDI and PLMI are maintained under 5 episodes per hour).

3. Subjects were determined to be free of medical conditions which would interfere with or be exacerbated by administration of GHB. This assessment will be based on medical history, physical examination and laboratory analyses.

4. In accordance with the Code of Federal Regulations 21 CFC Ch. 1 (Apr. 4, 1995 edition) Part 50, Subpart B, informed consent was obtained from each subject after the purpose and nature of this study, as well as the benefits and risks, have been explained.

B. Exclusion Criteria

A subject with any of the following were excluded from study participation:

1. A history of drug addiction, alcoholism, or drug abuse within the last year, or the regular use of two or more drinks daily.

2. The presence of any disorder or the regular use of any medication that could interfere with the absorption and/or metabolism of test medication, as determined by the investigator.

3. The presence of any disorder or the regular use of any medication that could interfere with the evaluation of the effectiveness of the test medication, as determined by the investigator.

4. Pregnant or lactating females were excluded.

5. History of exaggerated response or hypersensitivity to gammahydroxybutyrate or to other hypnotics.

6. History of seizures or serious head injury.

7. Use of any investigational drug within 30 days prior to screening visit.

C. Treatment Criteria

After keeping a sleep and pertinent symptom diary and recording miscellaneous adverse events for two weeks prior to the first treatment night, subjects began treatment if the following criteria were met:

1. The subject continued to meet the inclusion/exclusion criteria.

2. A night of diagnostic polysomnography has confirmed the absence or adequate control of periodic limb movement syndrome and sleep apnea.

3. Laboratory analyses revealed no abnormalities which may require clinical intervention, as determined by the investigator.

4. Treatment was discontinued if the subject demonstrated hypersensitivity to GHB during the first treatment night.

II. STUDY PROCEDURE

A. Baseline Period Evaluations

Prior to initiation of any of the following procedures, the study was explained, questions answered, and written informed consent obtained. Within four weeks prior to the first treatment night, each subject obtained and supplied to the investigator a recent complete medical history and physical examination. At least two weeks prior to the first treatment night, subjects kept diaries describing their sleep, their drug use and incidence and severity of their chronic fatigue syndrome or fibromyalgia symptoms.

B. Pre-Treatment Polysomnographic Evaluations

Prior to the first treatment night, a night of diagnostic polysomnography ruled out the possibility of sleep apnea or other sleep disorders which may cause excessive daytime sleepiness. This evaluation took place on the night prior to the first treatment night.

C. Treatment Phase

Prior to the first treatment night, an assessment was made as to the subject's continued qualification for participation. After these assessments were completed, the first treatment was administered at The Center For Research In Sleep Disorders, Cincinnati, Ohio, where subjects were polysomnographically monitored throughout the night. Subjects received 15 ml of fluid containing 2.25 grams of GHB at bedtime. To prevent the risk of injury from possible falls due to the rapid onset of sleep, the drug was administered to subjects already in bed. A second dose of 2.25 g of GHB was administered four hours later. Subjects were required to stay in bed for eight hours. The total dosage on this night did not exceed 4.5 grams.

A repeat polysomnography was carried out at the end of one month of nightly treatment.

Following the first night of treatment, each patient was given a three-month supply of the drug to be self-administered at home. Subjects continued to keep daily diaries identical to those completed during the baseline period. In some cases, a third dose of 10 ml may be administered if subjects cannot sleep during the final two hours of the eight-hour period. For most patients, the total nightly dose did not exceed 7 grams, and most patients maintained a 4.5 g nightly dose. Those subjects who are taking other medications as treatment for their condition were gradually withdrawn from those medications based on an individualized schedule determined by the investigator. Patients with a history of depression, however, were maintained on existing anti-depressant treatments. At the follow-up visit, safety and efficacy assessments were conducted.

III. EVALUATION METHODS—STUDY SPECIFIC

A. Polysomnography

An overnight polysomnogram was used to eliminate the possibility of other sleep-related disorders (especially sleep apnea and periodic limb movements in sleep) as cause for or as an exacerbating factor in excessive daytime sleepiness and fatigue. The polysomnographic recording was evaluated for sleep efficiency, sleep staging, and presence of disturbances.

B. Daily Diaries

Each subject completed a diary detailing nightly sleep latency, nighttime awakenings, quality of sleep, total sleep time, fatigue levels, number of daytime sleepy periods and levels of daytime alertness, location and intensity of pain and use of concomitant medications. Subjects recorded the dates of new bottle openings, and identified each new bottle of GHB by preparation date. All subjects recorded their weight at month end, and female subjects indicated days of menstruation.

IV. STUDY DRUGS AND SUPPLIES

A. Dosing and Dispensing

Subjects were provided a three-month supply of sodium oxybate (GHB). The lot number and date of preparation was recorded. Subjects self-administered a dose set by the investigator. A typical dose was 15 ml (made of 150 mg of GHB per ml of solution in distilled $H_2O$) immediately before lights out and again four hours later (total dose=4.5 g/night). Some subjects took a third, smaller dose. All doses for a given night were measured before the initial dose was taken. Subjects recorded the dose taken each night, specifying any derivations from the prescribed dose. When subjects opened a new bottle of GHB, they recorded the preparation date (which allowed tracking of bulk drug lot number and solution preparation information) on the daily diary.

V. RESULTS

Subjective recordings of all symptoms while taking the study medication were compared to baseline information. The primary outcome measures were the degree of fatigue, sleepiness and pain. Clinical laboratory evaluations and adverse events were monitored and used for an assessment of the risk factors involved in chronic use of GHB as a treatment for chronic fatigue syndrome and fibromyalgia. The results obtained following a one-month course of treatment are summarized on Table 1, below.

TABLE 1

Treatment of FMS and CFS with GHB

| | Baseline | | Time Period | | | |
|---|---|---|---|---|---|---|
| | 2 weeks | 1 week | | | | |
| Patient | prior to test period | prior to test period | 1 week on GHB | 2 weeks on GHB | 3 weeks on GHB | 4 weeks on GHB |
| I. Fatigue | | | | | | |
| P1 | 3 | 4 | 7 | 7 | 5 | 6 |
| P2 | 5 | 3 | 8 | 7 | 8 | 9 |
| P3* | 2 | 2 | 4 | 6 | 5 | 7 |
| P4 | 2 | 2 | 4 | 5 | 6 | 7 |
| II. Pain | | | | | | |
| P1 | 3 | 4 | 7 | 7 | 6 | 7 |
| P2 | 4 | 7 | 7 | 7 | 9 | 9 |
| P3* | 4 | 5 | 8 | 7 | 7 | 8 |
| P4 | 2 | 3 | 3 | 6 | 6 | 6 |

| Patient | End of Two-Week Baseline | 4 Weeks on GHB |
|---|---|---|
| III. Overall Feelings of Well-Being | | |
| P1 | 3 | 8 |
| P2 | 6 | 7 |
| P3* | 2 | 5 |
| P4 | 4 | 7 |
| IV. Percent of Alpha Slow Waves During Slow Wave Sleep | | |
| P1 | 60 | 12 |
| P3* | 65 | 37 |

*P3 also presented with CFS; fatigue, pain and well-being were scored 1–10 with 10 being no pain, no fatigue and a high level of feelings of well-being. In IV, low alpha wave activity indicates restful sleep, e.g. low levels of NREM sleep.

As demonstrated by the data summarized on Table 1, all of the patients exhibited subjective improvement in intensity of fatigue, pain and feelings of well-being as compared to their ratings prior to entry into the study. Furthermore, the decreased percentage of alpha slow waves observed during slow wave sleep indicated that the quality of their sleep had improved.

All publications, patents, and patent applications mentioned in this specification are indicative of the level of ordinary skill in the art to which this invention pertains. All publications, patents, and patent applications are herein incorporated by reference to the same extent as if each individual publication or patent application was specifically and individually indicated to be incorporated by reference.

It will be apparent to one of ordinary skill in the art that many changes and modifications can be made in the invention without departing from the spirit or scope of the appended claims.

What is claimed is:

1. A therapeutic method comprising treating fibromyalgia syndrome by administering to a human in need of said treatment an effective amount of a compound of formula (I):

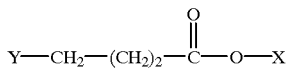

(I)

wherein X is H, a pharmaceutically acceptable cation or $(C_1-C_4)$alkyl, and Y is OH, $(C_1-C_4)$alkoxy, $(C_1-C_4)$alkanoyloxy or benzoyloxy wherein the amount is effective to alleviate symptoms.

2. A therapeutic method comprising treating chronic fatigue syndrome by administering to a human in need of said treatment an effective amount of a compound of formula (I):

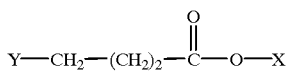

(I)

wherein X is H, a pharmaceutically acceptable cation or $(C_1-C_4)$alkyl, and Y is OH, $(C_1-C_4)$alkoxy, $(C_1-C_4)$alkanoyloxy or benzoyloxy.

3. The method of claim 1 or 2 wherein Y is OH or $(C_1-C_4)$alkanoyloxy.

4. The method of claim 3 wherein X is a pharmaceutically acceptable cation.

5. The method of claim 4 wherein X is $Na^+$.

6. The method of claim 1 or 2 wherein Y is OH and X is $Na^+$.

7. The method of claim 1 or 2 wherein the compound of formula (I) is administered orally, in combination with a pharmaceutically acceptable carrier.

8. The method of claim 7 wherein the carrier is a liquid.

9. The method of claim 7 wherein the carrier is a tablet or capsule.

10. The method of claim 1 or 2 wherein a daily dose of about 1–500 mg/kg is administered.

11. The method of claim 1 or 2 wherein a daily dosage of about 0.5–20 g is administered.

12. The method of claim 1 or 2 wherein the compound of formula (I) is administered parenterally, in combination with a pharmaceutically acceptable carrier.

13. The method of claim 12 wherein the compound is administered by injection or infusion.

14. The method of claim 12 wherein the compound is administered by inhalation.

15. The method of claim 12 wherein the compound is administered by means of a transdermal patch.

* * * * *